(12) United States Patent
Bates et al.

(10) Patent No.: US 11,383,025 B2
(45) Date of Patent: Jul. 12, 2022

(54) DUAL CHAMBER AND GEAR PUMP ASSEMBLY FOR A HIGH PRESSURE DELIVERY SYSTEM

(71) Applicant: Becton, Dickinson and Company, Franklin Lakes, NJ (US)

(72) Inventors: James Bates, Sparta, NJ (US); Robert Banik, Edgewater, NJ (US); Barry Ginsberg, Wyckoff, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 246 days.

(21) Appl. No.: 16/405,037

(22) Filed: May 7, 2019

(65) Prior Publication Data
US 2019/0255250 A1 Aug. 22, 2019

Related U.S. Application Data

(60) Division of application No. 14/478,837, filed on Sep. 5, 2014, now Pat. No. 10,314,967, which is a
(Continued)

(51) Int. Cl.
*A61M 5/142* (2006.01)
*F04C 14/20* (2006.01)
(Continued)

(52) U.S. Cl.
CPC ...... *A61M 5/14216* (2013.01); *A61M 5/1424* (2013.01); *A61M 5/14236* (2013.01);
(Continued)

(58) Field of Classification Search
CPC .. A61M 2005/3128; A61M 2005/3152; A61M 5/14216; A61M 5/14236;
(Continued)

(56) References Cited

U.S. PATENT DOCUMENTS 1,646,374 A * 10/1927 Wilkin ............... F16H 55/08
74/462
2,897,765 A * 8/1959 Kitano ............... F01C 1/126
418/206.5

(Continued)

FOREIGN PATENT DOCUMENTS

DE 35 15 624 A1 11/1986
EP 1363025 B1 11/2003
(Continued)

OTHER PUBLICATIONS

European Search Report for Application No. 09798312.6-2320/2303362, PCT/US2009/004132 dated May 16, 2012.
(Continued)

*Primary Examiner* — Quynh-Nhu H. Vu
(74) *Attorney, Agent, or Firm* — Dickinson Wright PLLC

(57) ABSTRACT

A high pressure delivery system for delivering a medicament, comprising a first chamber for storing a supply of the medicament, a gear pump assembly in fluid communication with the first chamber, said gear pump assembly having a dose inlet and a dose discharge, said dose inlet having a larger diameter than said dose discharge to provide a high pressure discharge, and a fluid connection path in fluid communication with the gear pump assembly for delivering the medicament to a high pressure area.

8 Claims, 16 Drawing Sheets

Related U.S. Application Data continuation of application No. 12/737,447, filed as application No. PCT/US2009/004132 on Jul. 17, 2009, now Pat. No. 8,905,970.

(60) Provisional application No. 61/082,053, filed on Jul. 18, 2008.

(51) Int. Cl.
| | |
|---|---|
| *A61M 5/155* | (2006.01) |
| *F04C 2/08* | (2006.01) |
| *F04C 2/14* | (2006.01) |
| *A61M 5/168* | (2006.01) |
| *A61M 5/20* | (2006.01) |
| *A61M 5/24* | (2006.01) |
| *A61M 5/31* | (2006.01) |
| *A61M 5/315* | (2006.01) |
| *A61M 5/48* | (2006.01) |

(52) U.S. Cl.
CPC ........ *A61M 5/14244* (2013.01); *A61M 5/155* (2013.01); *F04C 2/084* (2013.01); *F04C 2/14* (2013.01); *F04C 14/20* (2013.01); *A61M 5/16809* (2013.01); *A61M 5/204* (2013.01); *A61M 5/2053* (2013.01); *A61M 5/24* (2013.01); *A61M 5/3146* (2013.01); *A61M 5/31535* (2013.01); *A61M 5/31585* (2013.01); *A61M 5/482* (2013.01); *A61M 5/484* (2013.01); *A61M 2005/3128* (2013.01); *A61M 2005/3152* (2013.01); *F04C 2220/24* (2013.01)

(58) Field of Classification Search
CPC ............ A61M 5/1424; A61M 5/14244; A61M 5/155; A61M 5/16809; A61M 5/204; A61M 5/2053; A61M 5/24; A61M 5/3146; A61M 5/31535; A61M 5/31585; A61M 5/482; A61M 5/484; F04C 2/084; F04C 2/14; F04C 2/20; F04C 2220/24
See application file for complete search history.

(56) References Cited

U.S. PATENT DOCUMENTS

| | | | |
|---|---|---|---|
| 3,057,370 A | 10/1962 | Hamilton | |
| 3,218,984 A * | 11/1965 | Mosovsky | F01C 1/20 418/188 |
| 3,306,228 A * | 2/1967 | Drutchas | F04C 2/344 418/192 |
| 3,817,117 A * | 6/1974 | Kita | F04C 2/084 74/462 |
| 4,106,361 A * | 8/1978 | Burtis | B23F 5/12 74/462 |
| 4,130,383 A * | 12/1978 | Moinuddin | F04C 2/088 418/189 |
| 4,210,173 A | 7/1980 | Choksi et al. | |
| 4,253,501 A | 3/1981 | Ogle | |
| 4,356,727 A | 11/1982 | Brown et al. | |
| 4,548,562 A * | 10/1985 | Hughson | F04C 2/16 418/201.3 |
| 4,623,301 A | 11/1986 | Reynolds | |
| 4,645,496 A | 2/1987 | Oscarsson | |
| 4,852,352 A | 8/1989 | Leigh-Monstevens | |
| 4,905,730 A | 3/1990 | Stoll | |
| 4,915,688 A | 4/1990 | Bischof et al. | |
| 5,002,528 A | 3/1991 | Palestrant | |
| 5,246,358 A * | 9/1993 | Gu | F04C 2/20 418/191 |
| 5,439,452 A | 8/1995 | McCarty | |
| 5,406,228 A | 11/1995 | Evans | |
| 5,466,228 A | 11/1995 | Evans | |
| 5,472,403 A | 12/1995 | Comacchia | |
| 5,600,951 A * | 2/1997 | Helver | F16H 39/42 60/398 |
| 5,807,312 A | 9/1998 | Dzwonkiewicz | |
| 5,823,991 A | 10/1998 | Shim | |
| 5,911,708 A | 6/1999 | Teirstein | |
| 6,048,186 A * | 4/2000 | Kitano | G01F 3/10 73/261 |
| 6,099,511 A | 8/2000 | Devos et al. | |
| 6,283,734 B1 * | 9/2001 | Blume | F04C 2/086 418/206.4 |
| 6,582,387 B2 | 6/2003 | Derek et al. | |
| 6,853,450 B1 | 10/2005 | Baldwin et al. | |
| 7,014,436 B2 * | 3/2006 | Klassen | F04C 2/084 418/206.5 |
| 7,056,307 B2 | 6/2006 | Smith et al. | |
| 7,232,428 B1 | 6/2007 | Inukai et al. | |
| 7,677,526 B2 | 3/2010 | Lymberopoulos | |
| 7,695,445 B2 | 4/2010 | Yuki | |
| 7,704,236 B2 | 4/2010 | Denolly | |
| 8,052,856 B2 | 11/2011 | Dorsey | |
| 8,211,091 B2 | 7/2012 | Guzman | |
| 8,328,787 B2 | 12/2012 | Guzman | |
| 8,444,594 B2 | 5/2013 | Schweiger | |
| 8,689,893 B2 | 4/2014 | Soltvedt | |
| 8,905,970 B2 | 12/2014 | Bates et al. | |
| 2002/0107501 A1 | 8/2002 | Smith et al. | |
| 2002/0151854 A1 | 10/2002 | Duchon et al. | |
| 2004/0082904 A1 | 4/2004 | Houde et al. | |
| 2004/0089050 A1 | 5/2004 | Daw et al. | |
| 2004/0166010 A1 * | 8/2004 | Lafferty | F04C 2/086 418/206.7 |
| 2004/0210162 A1 | 10/2004 | Wyatt et al. | |
| 2007/0060894 A1 | 3/2007 | Dai et al. | |
| 2007/0088252 A1 | 4/2007 | Prestotnik et al. | |
| 2007/0244435 A1 * | 10/2007 | Hicks | A61M 5/14236 604/131 |
| 2008/0167621 A1 | 7/2008 | Wagner et al. | |
| 2009/0035121 A1 * | 2/2009 | Watson | F01C 1/126 73/861.87 |
| 2009/0221914 A1 | 9/2009 | Barrett et al. | |
| 2010/0185040 A1 | 7/2010 | Uber et al. | |

FOREIGN PATENT DOCUMENTS

| | | | |
|---|---|---|---|
| FR | 1499582 A | 10/1967 | |
| JP | 6-23044 A | 2/1994 | |
| JP | 2002-511317 A | 4/2002 | |
| JP | 2005-508679 A | 11/2006 | |
| JP | 2006-526467 A | 11/2006 | |
| WO | WO-9601950 A1 * | 1/1996 | F04C 2/084 |
| WO | 2003-067091 A1 | 8/2003 | |
| WO | 2006-032070 A1 | 3/2006 | |
| WO | 2006-123329 A2 | 11/2006 | |
| WO | 2007-117967 A2 | 10/2007 | |

OTHER PUBLICATIONS

Anonymous, Gear Pump, Wikipedia, the free encyclopedia, Feb. 6, 2005, http://en.wikipedia.org/wiki/File: Gear_pump.png.
Notice of Rejection dated Jul. 20, 2013 issued by the Japanese Patent Office in counterpart Japanese Application No. 2011-518736.
European Search Report for Application No. EP 11169439 dated May 16, 2012.

* cited by examiner

EXAMPLE HYDRAULIC ADVANTAGE          USER INPUT, F=4 LBS.

| 'D' | $A=PI\ (D/2)^2$ | $P=F/A$ | 'd' | $A=PI\ (D/2)^2$ | $P=F/A$ |
|---|---|---|---|---|---|
| 0.375" | 0.11 in$^2$ | 36.4 PSI | .18 | .0254 IN$^2$ | 157 PSI |

$$\frac{157\ PSI}{54\ PSI} = 2.9\ X\ PRESSURE\ OUTPUT$$

FIG.9

ROTATION TO TURN PUMP GEARED FROM PRESSING PLUNGER

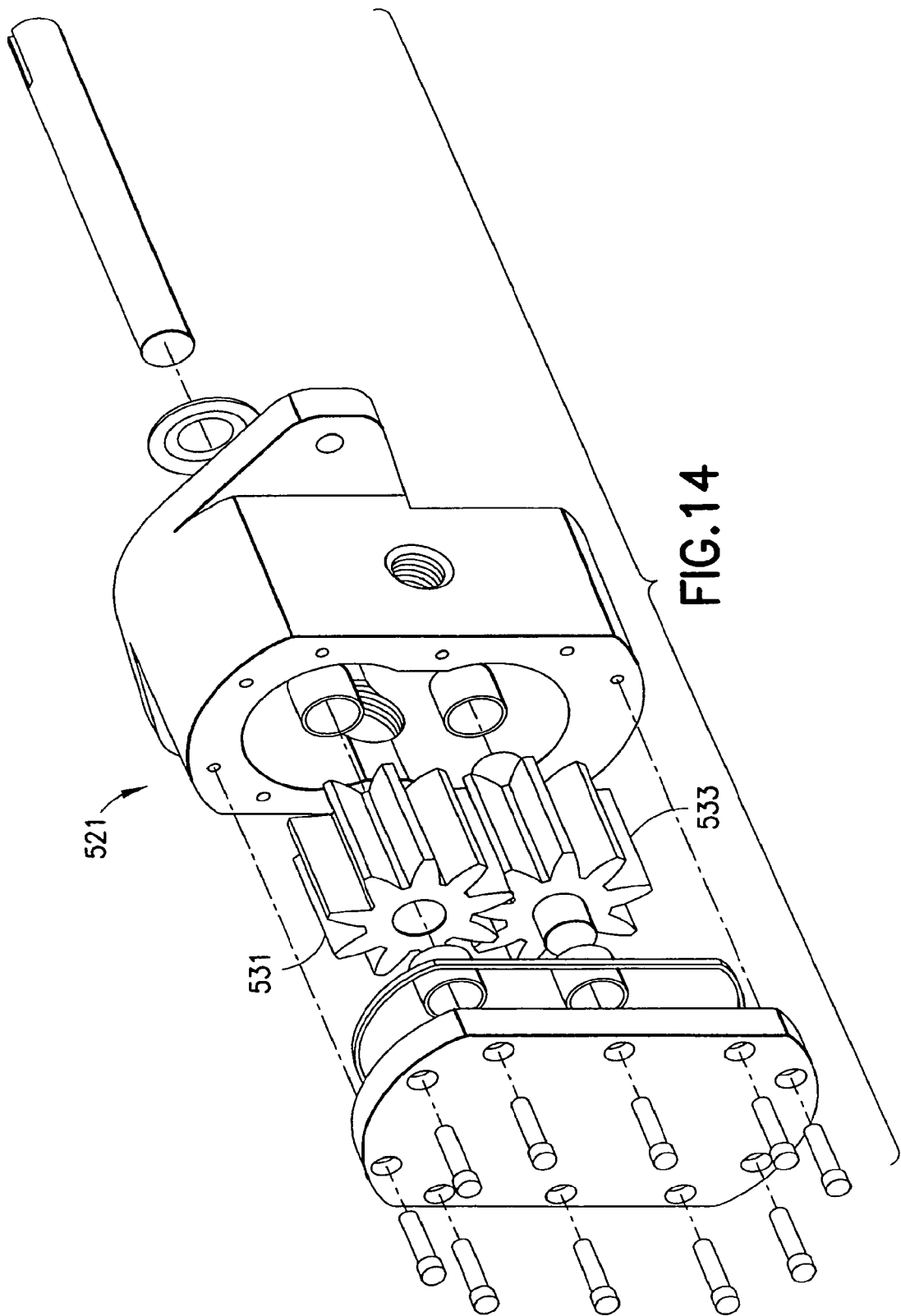

| TOOTH POSITION # | VOLUME DISPENSED (UNITS) |
|---|---|
| PRIME | PRIME |
| 1 | 1 |
| 2 | 1 |
| 3 | 1 |
| 4 | 1 |
| 5 | 1 |
| 6 | 1 |
| 7 | 1 |
| 8 | 1 |
| 9 | 1 |
| 10 | 1 |
| 11 | 1 |
| 12 | 1 |
| 13 | 1 |
| 14 | 1 |
| 15 | 1 |
| 16 | 1 |
| 17 | 1 |
| 18 | 1 |

MAXIMUM DOSE 18 UNITS EXAMPLE

CONSTANT RATE – CONSTANT GEAR TEETH

| TOOTH POSITION # | VOLUME DISPENSED (UNITS) |
|---|---|
| PRIME | PRIME |
| 1 | 0.2 |
| 2 | 0.2 |
| 3 | 0.2 |
| 4 | 0.2 |
| 5 | 0.2 |
| 6 | 0.5 |
| 7 | 0.5 |
| 8 | 0.5 |
| 9 | 0.5 |
| 10 | 0.5 |
| 11 | 0.5 |
| 12 | 0.5 |
| 13 | 0.5 |
| 14 | 1 |
| 15 | 1 |
| 16 | 1 |
| 17 | 1 |
| 18 | 1 |

MAXIMUM DOSE 10 UNITS EXAMPLE

DUAL CHAMBER AND GEAR PUMP ASSEMBLY FOR A HIGH PRESSURE DELIVERY SYSTEM

CROSS REFERENCE TO RELATED APPLICATION

This application is a division of U.S. patent application Ser. No. 14/478,837, filed Sep. 5, 2014, which is a continuation of U.S. patent application Ser. No. 12/737,447, filed Apr. 7, 2011, now U.S. Pat. No. 8,905,970, which is the U.S. National Stage of International Patent Application No. PCT/US2009/004132, filed on Jul. 17, 2009, which claims the benefit under 35 U.S.C. § 119(e) of U.S. Provisional Application Ser. No. 61/082,053, filed Jul. 18, 2008, the entire content of all said prior applications being hereby incorporated by reference.

FIELD OF THE INVENTION

The present invention relates to a high pressure delivery system for delivering a medicament. More particularly, the present invention relates to a high pressure drug delivery system that diverts high pressures away from the drug storing chamber to prevent medication leakage and inaccurate doses.

BACKGROUND OF THE INVENTION

In certain circumstances, it is desirable to inject medication directly into human tissue. Typically, syringes are used to inject medicaments into tissue areas, such as the intramuscular tissue layer, the subcutaneous tissue layer, and the intradermal tissue layer. Each of these tissue layers has specific characteristics that affect the amount of fluid pressure needed to inject a fluid into the targeted tissue layer. When injecting fluids into each of these tissue layers, the user must exert enough force on the injection device to overcome different amounts of backpressure associated with the particular tissue layer. In general, practitioners and self-injectors, such as diabetics, are familiar with the force necessary to inject fluids into the subcutaneous layer. Injections into the subcutaneous and intramuscular tissue layers can cause discomfort to the patient or self-injector because of the characteristics of the tissue, needle length and needle diameter or gauge. It is desirable to employ shorter, smaller gauge needles to achieve delivery into the intradermal tissue layer.

It is noted that when the needle lengths are shortened and needle diameters are made smaller, the fluid dynamics of the injection device changes. Additionally, the fluid dynamics between the injection device and the targeted tissue layer also change because the shorter needle length injects the fluid into a different tissue layer, such as the intradermal layer. Since the tissue density between the intramuscular, subcutaneous, and intradermal tissue layers varies, the ease with which fluid may be injected into each type of tissue layer varies. The variation in tissue density causes changes in the backpressure exerted by the tissue against the fluid when it is injected. For instance, the backpressure associated with the intradermal tissue layer is greater than the backpressure associated with the subcutaneous tissue layer, thereby requiring a higher pressure and a greater force to accomplish the injection.

Currently, several pen injection systems are commercially available for subcutaneous substance delivery of medication. These pen injection systems typically use 29 to 31 gauge needles having lengths of between 5 mm and 12.7 mm, and are used to deliver the contents of a medicament cartridge, such as insulin, to the subcutaneous tissue layers of a patient rapidly and conveniently. The medicament cartridges are generally of a standard volume and size (including a fixed cross sectional area). The pressure of delivery is the quotient of the actuation force exerted by a user and the cross sectional area of the cartridge. Since the cross-sectional area of the cartridge is fixed, higher delivery pressures require higher actuation forces by the user.

A "microneedle" pen system has been developed to facilitate subcutaneous substance delivery. Such "microneedle" drug delivery systems may include shorter needles, typically less than or equal to 3 mm, with smaller diameters, in the range of 30 to 34 gauge or thinner. Such needle length and gauge size combinations are desirable to provide for sharp, yet short, point geometries that can more accurately target substance delivery to only certain selected tissue, such as the deep intradermal or shallow subcutaneous tissue layers, thereby permitting controlled fluid delivery. Current typical pen injection systems used for subcutaneous delivery are not believed optimal for use by the general population of self-injectors for delivery into the intradermal layer because of, inter alia, the high backpressures associated with injecting fluid into the intradermal layers of the skin using microneedles.

To achieve effective medication delivery to the targeted tissue layer in light of higher backpressures, it is desirable to control two factors: the depth accuracy of the injection and the rate of the injection. This is of particular interest in connection with intradermal injections because the backpressures are relatively high, but similar analysis can be applied when injecting into the intramuscular or the subcutaneous tissue layers. The delivery of medicament within the narrow depth range of the intradermal tissue layer should first be assured, and maintained during injection. Once the depth accuracy is obtained, the rate of injection should be controlled to minimize or eliminate leakage of the medicament into other tissue layers or back out through the skin. Additional details of intradermal drug delivery and microneedles have been previously described in U.S. Pat. No. 6,494,865, issued on Dec. 17, 2002, U.S. Pat. No. 6,569,143, issued on May 27, 2003, PCT Publication No. WO2005025641, published Mar. 24, 2005, and U.S. Patent Application Publication No. 2005/0065472, published on Mar. 24, 2005, all of which are assigned to Becton, Dickinson and Company, and the entire content of each such patent and application being incorporated herein by reference.

The intradermal tissue layer of the skin is considerably denser than the subcutaneous tissue region. The density of the intradermal tissue layer on a particular patient is, in part, a function of their collagen make-up, which is affected by the patient's age, and the location of the injection site on the patient's body. This increased density of the intradermal tissue layer can create a greater backpressure resistance on the injection device than the resistance created when injecting into the subcutaneous tissue region. To overcome the increased backpressure resistance when injecting into the intradermal tissue layer with a conventional drug delivery pen, the user or patient would need to exert greater actuation force (which could be substantial) on the injector device actuator or employ some sort of powered injector device. In these applications, the injector device must be designed to withstand the greater backpressure from the intradermal injection site as well as the additional force exerted by the user or patient. Further, the increased actuation force required to actuate the injector device may result in the fluid "jetting" past the desired tissue depth due to the increased fluid pressure.

Conventional drug delivery pens may require that the user keep the needle seated in the skin for a period of up to about 10 seconds, after the injection has been completed, to allow for the "axial compliance" of the pen mechanism (or lead screw) and the cartridge back-end stopper to equilibrate to minimize "drool" from the needle tip upon withdrawal. Such time periods may need to be increased to accommodate any additional axial compliance resulting from higher backpressures, and such increased time periods can also decrease the required force to make the injection.

As advances in understanding the delivery of drug proceeds, the use of intradermal delivery systems is expected to increase. Use of a "standard" length needle to deliver a drug substance intradermally has its shortcomings, as noted above. It is not possible to use a delivery device having a needle length suited for intradermal injection to aspirate a syringe with drug substance from a multi-use vial. Thus, there are shortcomings in the prior art that prevent administering an intradermal injection using a "standard" length needle and a multi-use vial. It would be advantageous to have a drug delivery device capable of accessing substances stored in multi-dose vials and delivering such substances into the intradermal region of the skin without encountering the shortcomings described above.

Existing drug delivery pens offer several advantages over syringe based systems for delivering insulin subcutaneously. Reusable drug delivery pens hold 20 or more doses without requiring the drug cartridge to be refilled. Dose setting is achieved simply with the use of a dial. However, those drug delivery pens are designed for low pressure subcutaneous injections. Intradermal injection of insulin and other medications provides faster uptake of the drug, thereby leading to improved therapy. Existing drug delivery pens have several limitations regarding intradermal drug delivery. First, the mechanical advantage provided by the pen is minimal and requires the user to supply upwards of 20 lbs of force to generate sufficient pressure. Secondly, the pen components are often damaged by this high force, resulting in leaking and inaccuracy at the high pressures. Additionally, the size of the drug delivery pen required to obtain the high pressures associated with intradermal drug delivery would be too large for a user to conveniently carry.

There are no existing intradermal pen-like devices that take advantage of pen-like, dial-a-dose accuracy and ease of use with syringe like (small diameter) high pressure performance. Existing drug delivery pens require a large force to inject medication into the intradermal layer, thereby making the intradermal medication injection difficult. Furthermore, the drug delivery pen components are often damaged due to the high pressures, thereby resulting in medication leakage and dose inaccuracy.

Therefore, a need exists to provide a system and method for enabling users or patients to perform high pressure delivery of compounds, such as therapeutic drugs, vaccines, and diagnostic materials, at a controlled rate without requiring the exertion of an overly large force or resulting in an unwieldy device.

SUMMARY OF THE INVENTION

In accordance with an aspect of the present invention, a high pressure drug delivery system is provided that separates the dose setting mechanisms from the high pressure associated with drug delivery so that the stress caused by the high pressure does not affect the dose setting.

The accuracy of a pen's screw dose setting is combined with the hydraulic advantage of a small bore syringe to deliver medicaments in high pressure applications, such as an intradermal area. Valving between the cartridge and the syringe operates like a plunger-type reciprocating device with two check valves that allow flow into the syringe during dose setting and only allows flow through the microneedle during injection. The check valve allows a user to inject the dose from the syringe back into the cartridge when a user accidentally overdoses into the syringe.

In accordance with another aspect of the present invention, a high pressure drug delivery system is provided that uses a gear pump assembly to accomplish the high pressure drug delivery.

Other objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which:

FIG. 9 is a table of characteristics for a user input of four pounds;

FIG. 14 is a perspective view of an exemplary gear pump assembly of the high pressure delivery system of FIGS. 10 and 12;

Throughout the drawings, like reference numbers will be understood to refer to like parts, components and structures.

DETAILED DESCRIPTION OF THE EXEMPLARY EMBODIMENTS

Figure 1:
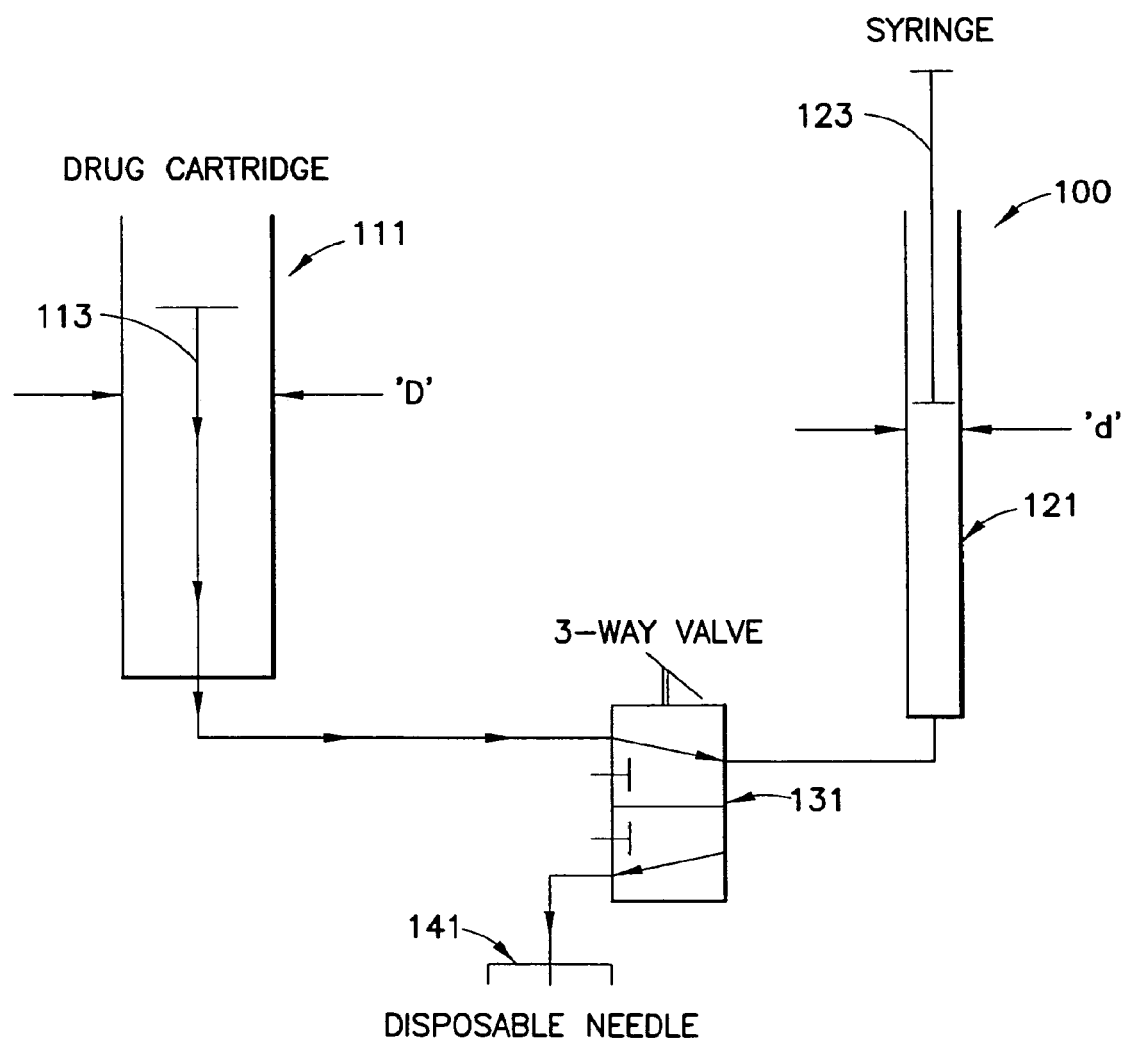
FIG. 1 is a schematic diagram of a dual chamber assembly for a high pressure delivery system having a 3-way valve according to an exemplary embodiment of the present invention.

An exemplary embodiment of the present invention includes a high pressure drug delivery system having a cartridge, which is preferably a typical 3 ml cartridge, coupled to a preferably disposable syringe that accommodates the high pressure generated from a small diameter syringe. The cartridge and syringe are coupled by a valving system that allows medicament to flow from the cartridge to the syringe and then prevents backflow during delivery of the medicament. The valving system may include 3-way valves, stopcock valves, or check valves, or any other suitable valve. The valving system prevents contamination of the stored medicament, which is a greater concern due to the use of a dual chamber system. An intradermal microneedle pen needle may be attached to the syringe and replaced with each use, thereby providing an interchangeable needle. The device may have a switch to allow the user to correct a dose without wasting the dose in the event that the dose is overdrawn.

To operate the high pressure drug delivery system, a user installs a cartridge or vial if it is a reusable product. Alternatively, the high pressure drug delivery system may be preconnected and is completely disposable. The user then sets or determines a dose, such as by dialing, in a manner similar to existing drug delivery pens. Depending on the valving system used, the user may need to set the proper valve position. The user injects the dose into the syringe located adjacent the pen cartridge or vial. As the dose enters the syringe, the plunger is pushed up. Alternatively, a single plunger may draw the dose into the syringe. A valving system allows flow from the cartridge or vial into the injection chamber of the syringe but does not allow backflow unless the user chooses to manually override the valve to allow backflow to reset or correct the dose. The user then connects any fluid connection path, such as microneedle, if it is not already connected. The fluid connection path, i.e., the needle, is then primed. The fluid connection path is then inserted into the area where the drug is to be delivered, such as the microneedle into an intradermal area, and the user depresses the syringe plunger to inject the dose.

In an exemplary embodiment of the present invention, the high pressure drug delivery system uses a microneedle and existing syringe or syringe components to generate the high pressure (approximately 200 psi) needed for intradermal delivery. The dose setting mechanism it separated from the high pressure so that the stress caused by the high pressure does not affect the dose setting. Existing dose setting/resetting mechanisms that are proven accurate, as well as commercially available cartridges (e.g., 3 ml cartridges), may be used to provide accurate doses for both small and large doses. Furthermore, the high pressure drug delivery system according to exemplary embodiments of the present invention may use conventional and completely disposable 3 ml cartridges with multiple microneedle pen needles, and may have a reusable dose setting (pen-like) and a valving system with a disposable syringe (using multiple microneedle pen needles) allowing for user installation of 3 ml cartridges. By using disposable parts, the high pressure drug delivery system is efficient and inexpensive.

An automatic priming feature allows the user to set the dose as in existing drug delivery pens, but also includes in the dose a priming dose. When the dose (dose plus priming dose) is transferred to the syringe, which is a limiting syringe that only allows the volume for the exact dose, the prime dose has nowhere to go but through a check valve and out through the fluid connection path, such as a needle, thereby automatically priming the high pressure drug delivery system.

FIGS. 1-4 are schematic diagrams of exemplary embodiments of high pressure drug delivery systems. As shown in FIGS. 1 and 5, the high pressure drug delivery system 100 includes a first chamber 111, a second chamber 121, a valving system 131 and a fluid connection path 141. The first chamber 111 may be a conventional 3 ml cartridge that stores the medicament to be delivered. Conventional 3 ml cartridges hold twenty (20) doses (15 unit average). The second chamber 121 may be a conventional syringe with a plunger 123. The fluid communication path 141 may be a disposable microneedle. The valving system 131 may be a 3-way valve in fluid communication with the first chamber 111, the second chamber 121 and the fluid communication path 141.

To use the high pressure drug delivery system 100 of FIGS. 1 and 5, the user sets the 3-way valve to the dose setting. The dose is then dialed using the thumbwheel of the cartridge and may be viewed through the dose window. The cartridge plunger 113 is then depressed to transfer the dose to the syringe, thereby causing the syringe plunger 123 to rise. The valve lever is then flipped to the inject setting. When the valve lever is in the inject setting, the valve prevents backflow of the dose to the cartridge. The user then uses the syringe plunger 123 to inject the dose. The valving system 131 prevents the first chamber 111 from seeing the high pressure associated with the drug delivery, thereby preventing dose inaccuracies, leakage and other problems associated with cartridges being exposed to high pressure.

Figure 6:
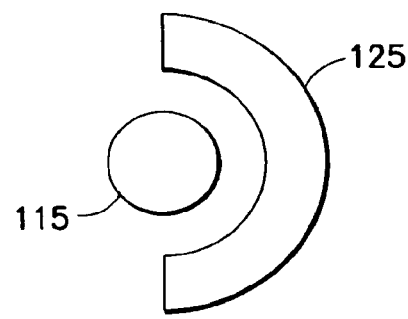
FIG. 6 is a top view of the schematic diagram of FIG. 5 showing an exemplary arrangement of the plungers.
Figure 7:
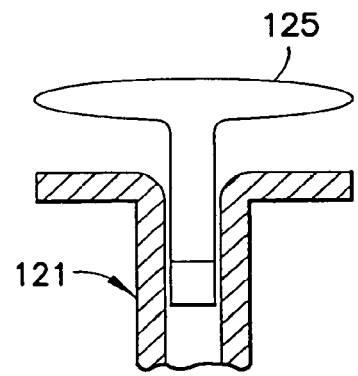
FIG. 7 is top view of the schematic diagram of FIG. 5 showing a plunger having a substantially T-shaped handle.

As shown in FIG. 6, the handle of the cartridge plunger 113 may be nested within the handle of the syringe plunger 123 to provide ergonomic operation. As shown in FIG. 7, the syringe plunger 123 may have a substantially T-shaped handle to increase the force acceptable to the user's hand.

Figure 2:
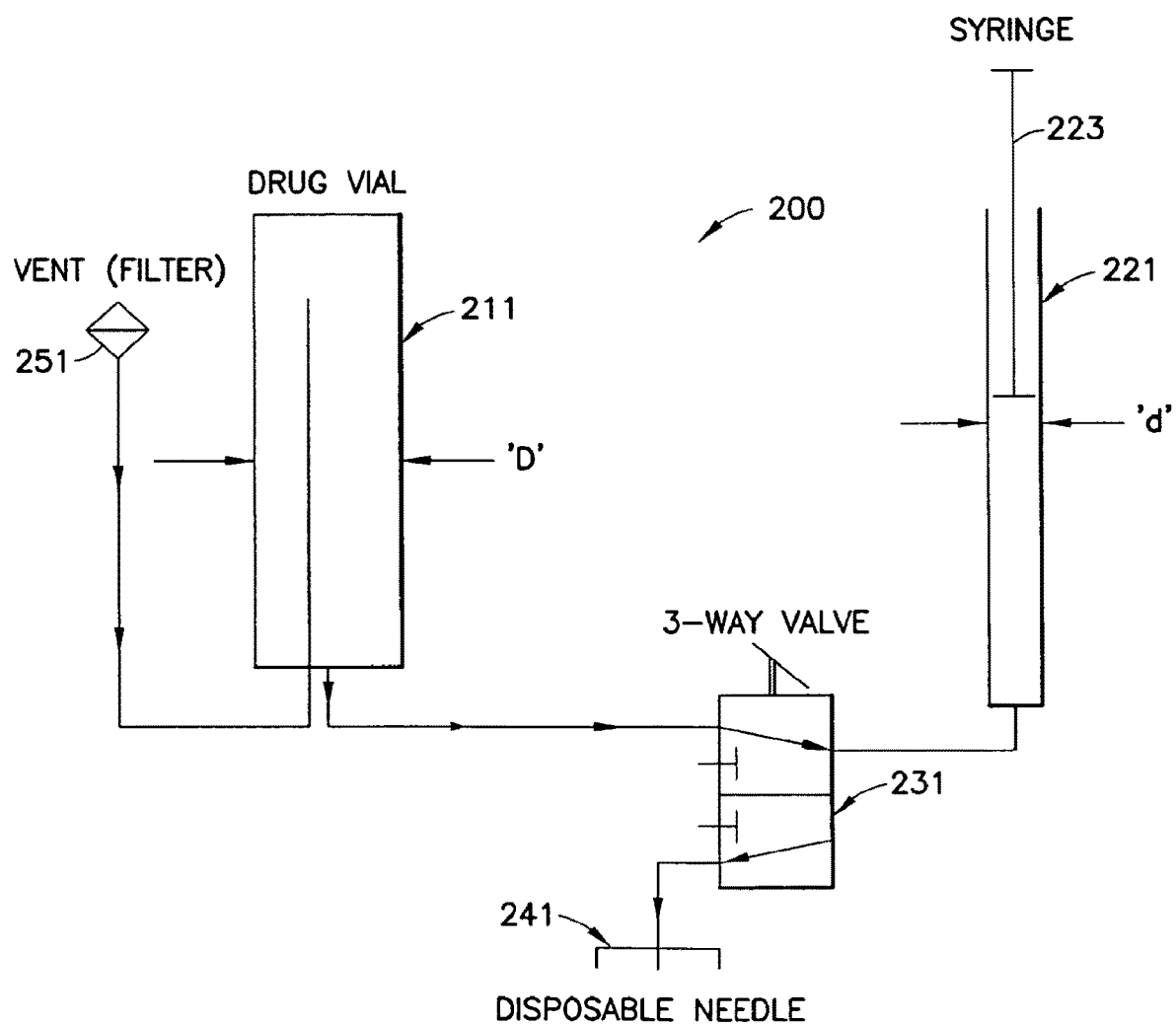
FIG. 2 is a schematic diagram of a dual chamber assembly for a high pressure delivery system having a 3-way valve and a vent according to another exemplary embodiment of the present invention.

As shown in FIG. 2, the high pressure drug delivery system 200 includes a first chamber 211, a second chamber 221, a valving system 231 and a fluid connection path 241. The first chamber 111 may be a conventional 10 ml drug vial that stores the medicament to be delivered. Conventional 10 ml drug vials contain approximately a 3-4 week supply of the medicament. The second chamber 221 may be a conventional syringe with a plunger 223. The fluid communication path 241 may be a disposable microneedle. The valving system 231 may be a 3-way valve in fluid communication with the first chamber 211, the second chamber 221 and the fluid communication path 141. Operation is similar to that of the high pressure drug delivery system of FIG. 1, except that the dose is set at the syringe and the syringe plunger 223 is withdrawn to draw the dose into the syringe. Additionally, a vent 251 is connected the first chamber 211 so when medicine exits the first chamber 211, the vent 251 allows air into the first chamber 211 to prevent a vacuum from being created. Conventional vials are closed containers without a moving stopper. The vent 251 prevents anything but air from entering the first chamber.

Figure 3:
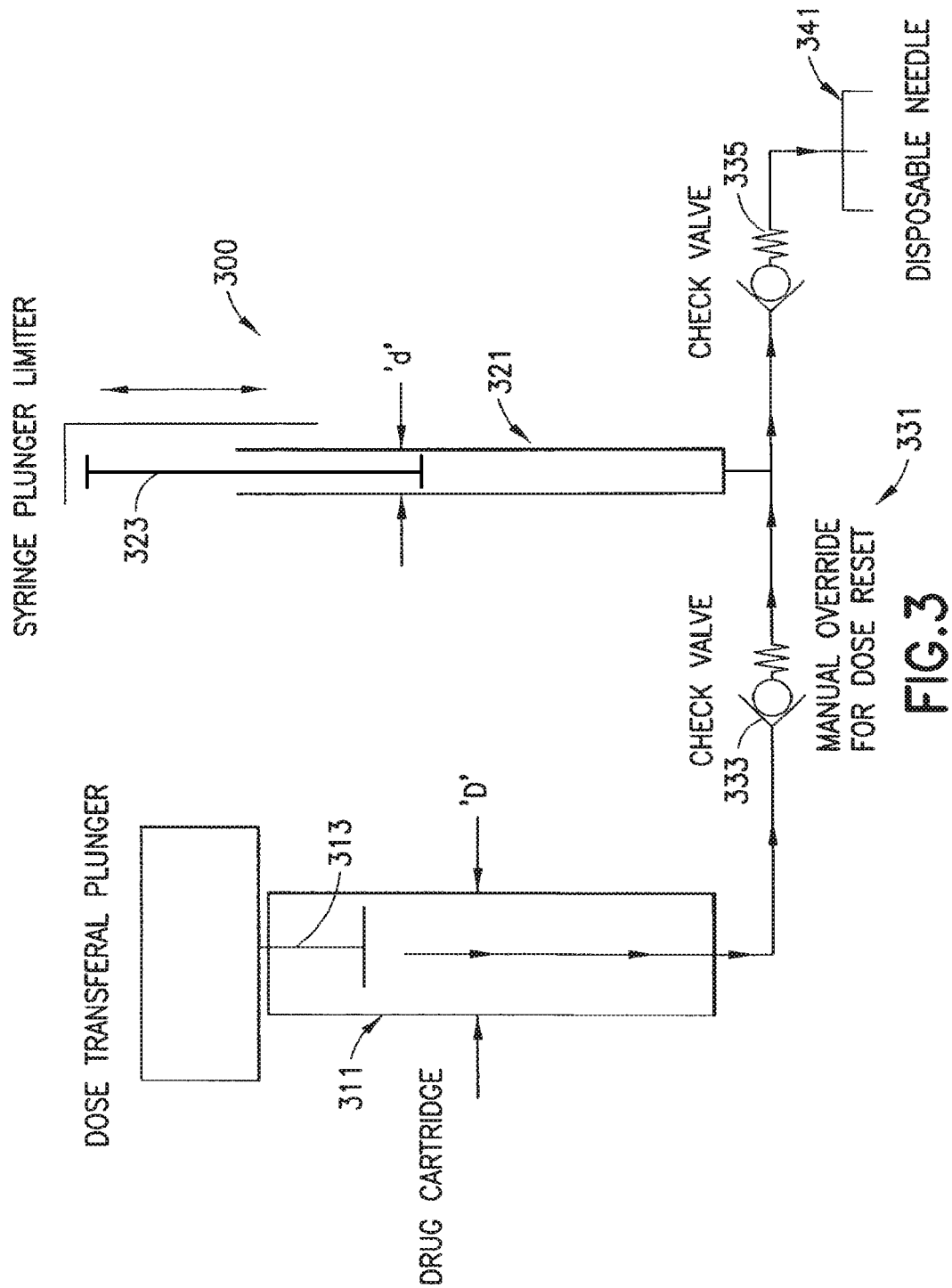
FIG. 3 is a schematic diagram of a dual chamber assembly for a high pressure delivery system having check valves according to another exemplary embodiment of the present invention.

As shown in FIG. 3, the high pressure drug delivery system 300 includes a first chamber 311, a second chamber 321, a valving system 331 and a fluid connection path 341. The first chamber 311 may be a conventional 3 ml cartridge that stores the medicament to be delivered. Conventional 3 ml cartridges hold twenty (20) doses (15 unit average). The second chamber 321 may be a conventional syringe with a plunger 323. The fluid communication path 341 may be a disposable microneedle. The valving system 331 may be a first check valve 333 disposed in fluid communication with the first chamber 311 and the second chamber 321 and a second check valve 335 in fluid communication with the second chamber 231 and the fluid communication path 341. The first check valve 333 may have a manual override to allow for dose correction or resetting.

To use the high pressure drug delivery system 300 of FIG. 3, the user dials the dose using the thumbwheel of the cartridge so that the dose may be viewed through the dose window. The cartridge plunger 313 is then depressed to transfer the dose to the syringe, thereby causing the syringe plunger 323 to rise. The first check valve 333 prevents backflow of the dose to the first chamber 311. The first check valve 333 may have a manual override to allow for dose correction or resetting. The user then uses the syringe plunger 323 to inject the dose through the second check valve 335 and through the fluid connection path 341. The valving system 331 prevents the first chamber 111 from seeing the high pressure associated with the drug delivery, thereby preventing dose inaccuracies, leakage and other problems associated with cartridges being exposed to high pressure.

As described above, the dose setting mechanism may set both the dose and the prime, thereby providing a self-priming system. When the dose is set, the second chamber 321 (the syringe) is set to only accept the dose and not the prime. The syringe may include a limiter that allows the syringe to only accept the dose amount. When the user pushes both the dose and the prime into the syringe injection chamber, the prime has nowhere to go but out through the second check valve 335 and through the fluid connection path 341, thereby priming the high pressure delivery system. Alternatively, the dose may be set on the syringe side to limit the stroke of the syringe.

Figure 4:
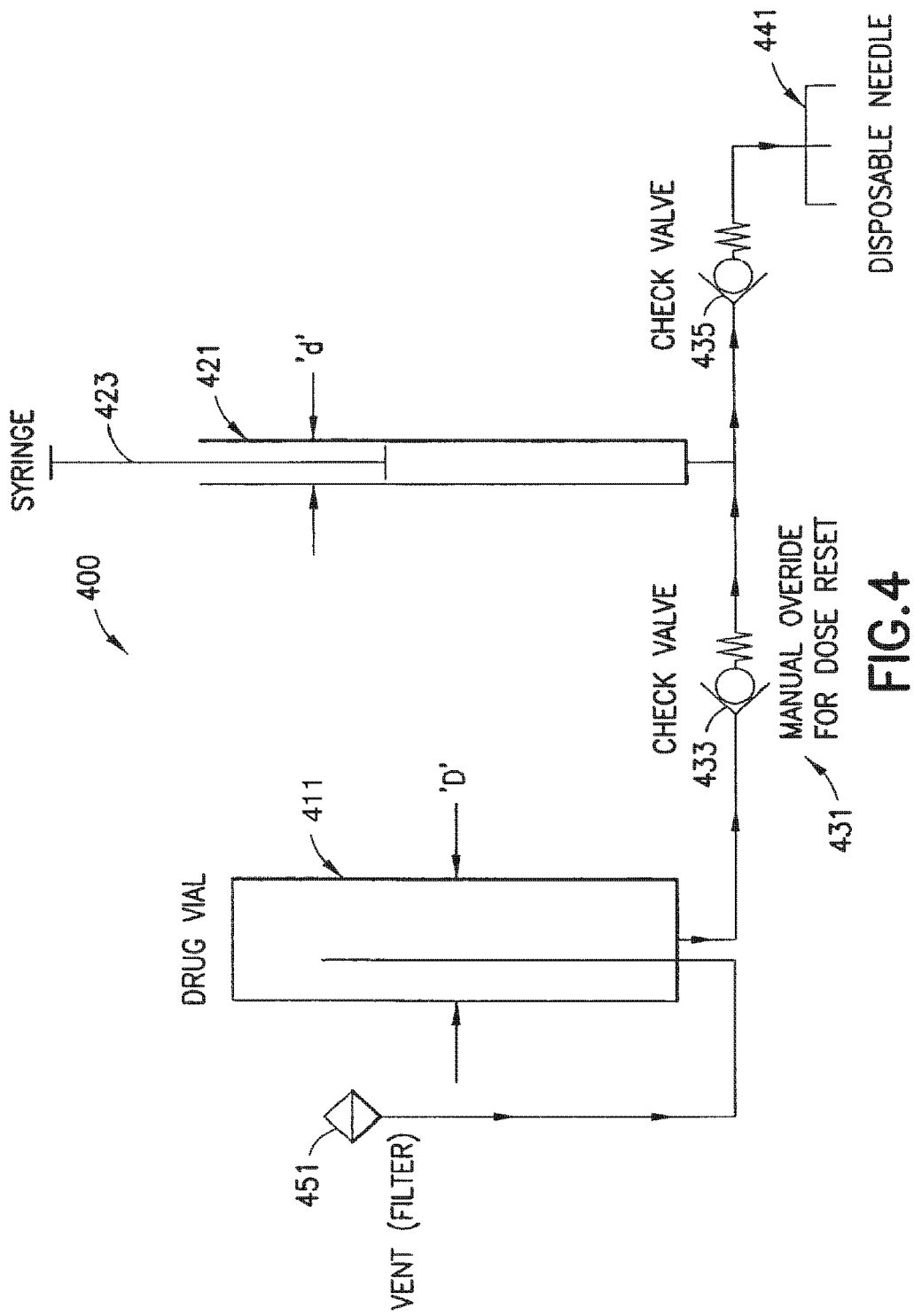
FIG. 4 is a schematic diagram of a dual chamber assembly for a high pressure delivery system having check valves and a vent connected to one of the chambers according to another exemplary embodiment of the present invention.
Figure 5:
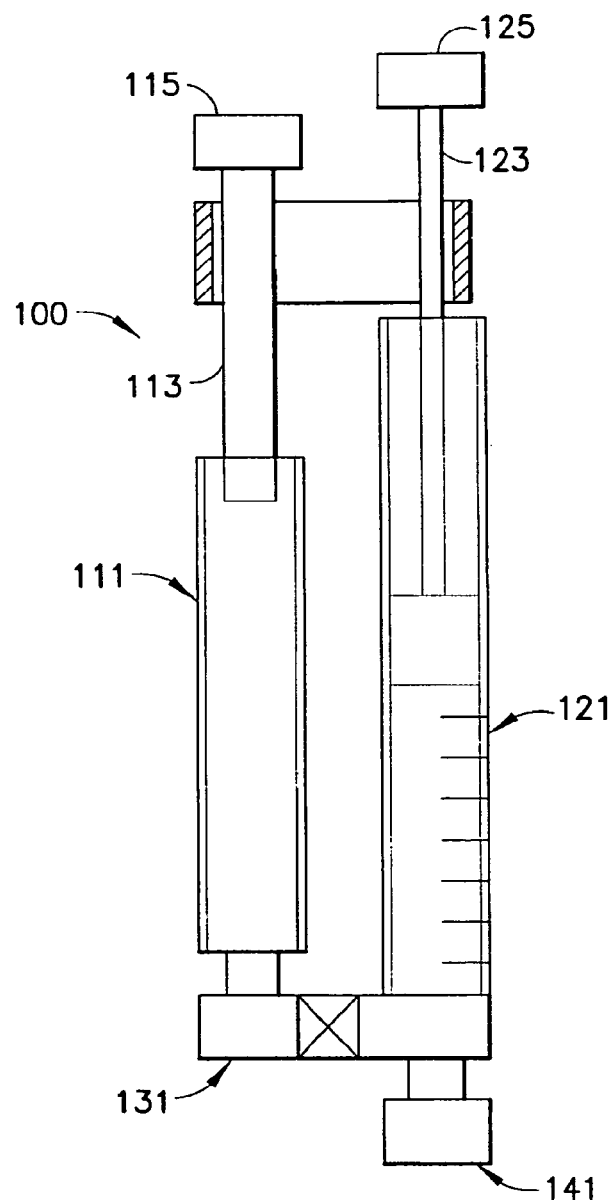
FIG. 5 is a schematic diagram of a dual chamber assembly for a high pressure delivery system having a plunger connected to both chambers according to another exemplary embodiment of the present invention.

As shown in FIG. 4, the high pressure drug delivery system 400 includes a first chamber 411, a second chamber 421, a valving system 431 and a fluid connection path 441. The first chamber 411 may be a conventional 10 ml drug vial that stores the medicament to be delivered. Conventional 10 ml drug vials contain approximately a 3-4 week supply of the medicament. The second chamber 421 may be a conventional syringe with a plunger 423. The fluid communication path 441 may be a disposable microneedle. The valving system 431 may be a first check valve 433 disposed in fluid communication with the first chamber 411 and the second chamber 421 and a second check valve 435 in fluid communication with the second chamber 431 and the fluid communication path 441. The first check valve 433 may have a manual override to allow for dose correction or resetting. Operation is similar to that of the high pressure drug delivery system of FIG. 3, except that the dose is set at the syringe and the syringe plunger 423 is withdrawn to draw the dose into the syringe. Additionally, a vent 451 is connected the first chamber 411 so when medicine exits the first chamber 411, the vent 451 allows air into the first chamber 411 to prevent a vacuum from being created. Conventional vials are closed containers without a moving stopper. The vent 451 prevents anything but air from entering the first chamber.

As shown in FIGS. 2 and 4, a vial-based system may be used with the high pressure drug delivery system. For example, the vial may have a volume of 10 ml, thereby providing approximately a 3-4 week supply of insulin to the user. Pre-filled vials are more readily available and less expensive than cartridges. Additionally, a plunger check valve may be used with a vial-based system.

Figure 8:
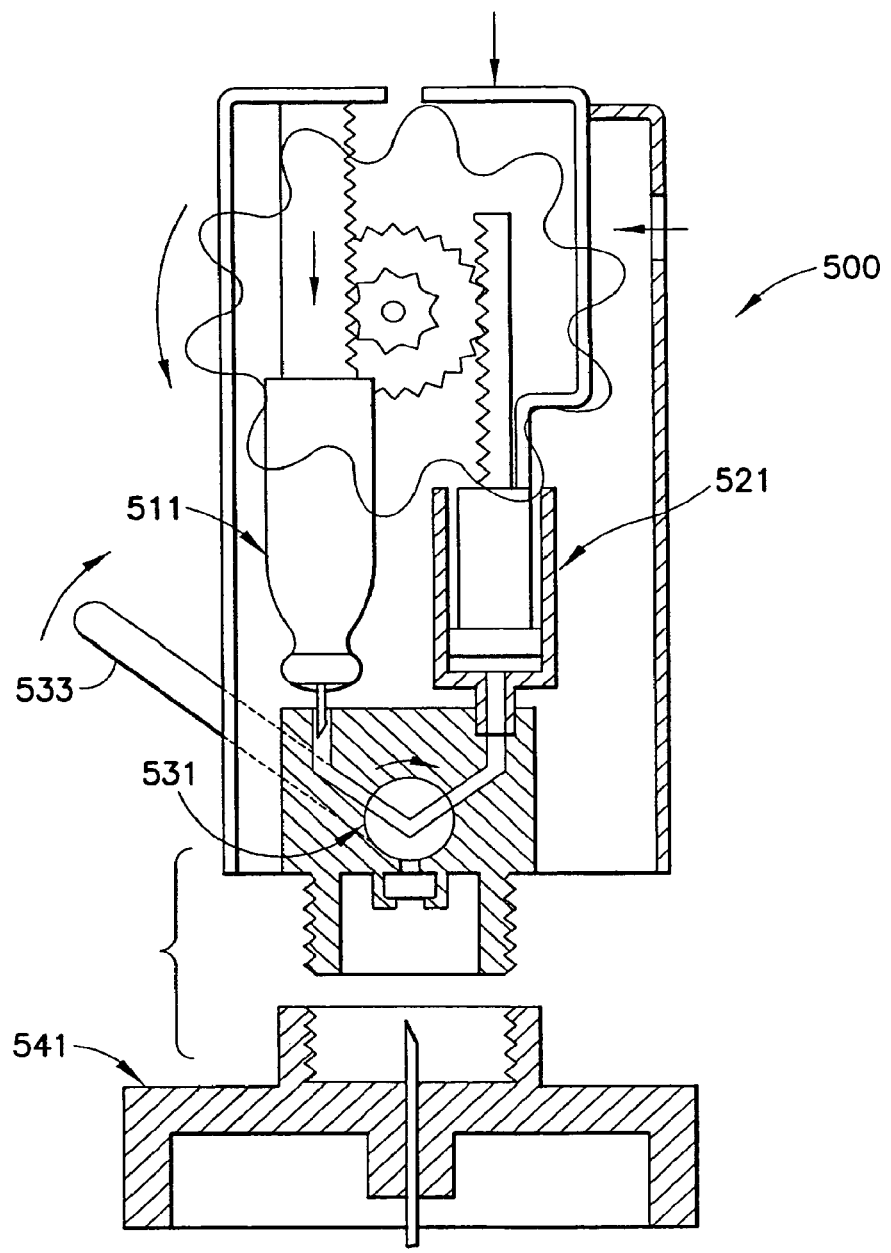
FIG. 8 is a schematic diagram of a dual chamber assembly for a high pressure delivery system according to another exemplary embodiment of the present invention.

In another exemplary embodiment of the high pressure drug delivery system 500 using vial-based delivery as shown in FIG. 8, the valving system 531 may be a manual switch check valve disposed in fluid communication between the first chamber 511 (vial) and the second chamber 521 (syringe). To operate the high pressure drug delivery system 500, the user first sets the check valve to the "set dose" setting using the lever 533. Air is then drawn into the syringe in an amount substantially equivalent to the dose size. The air is then injected into the vial. The check valve is then switched to the "inject" setting using the lever 533. The dose is then redrawn into the syringe, which now only includes insulin. The dose may then be delivered to the user.

When the check valve is set to the "set dose" mode, the check valve prevents flow into the syringe. The check valve that is open to air then cracks open under the vacuum, thereby drawing air into the syringe through the check valve. The drawn in air is then injected through the manual switch check valve into the vial, thereby pressurizing the vial with that "dose of air." When the manual switch check valve is switched to the "inject" mode, the syringe may be reloaded with the dose, which is now only insulin. Switching the valve to the "inject" mode reverses the check valve orientation, i.e., the direction of flow. Both check valves now only allow flow out of the syringe through the fluid connection path 541 (microneedle) so that the drug delivery may be made.

As shown in FIG. 9, for a given diameter "D" first chamber and a given diameter "d" second chamber, the required characteristics to accomplish a high pressure drug delivery with a user input of four pounds are provided.

Figure 10:
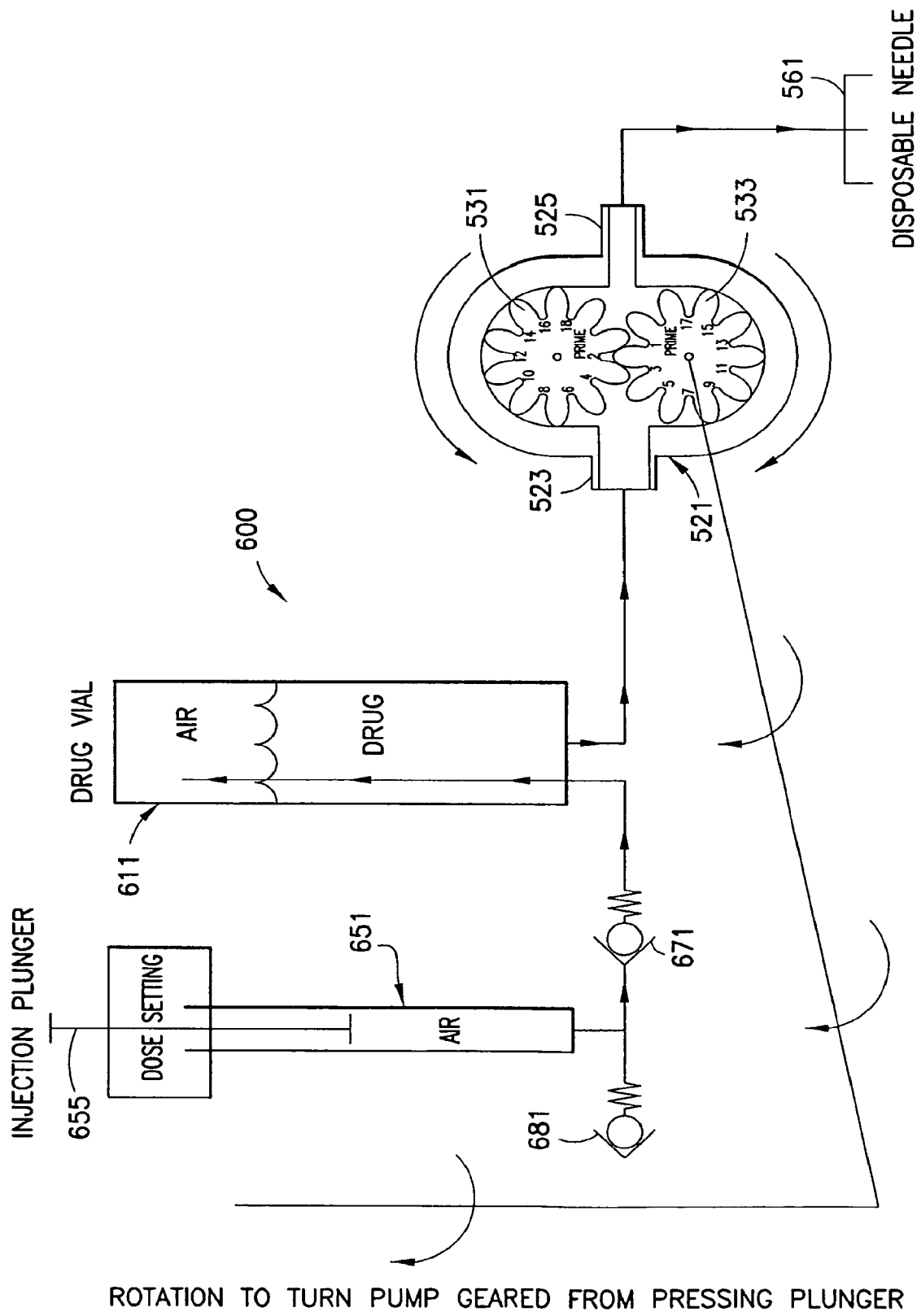
FIG. 10 is a schematic diagram of a gear pump assembly for a high pressure delivery system according to an exemplary embodiment of the present invention.
Figure 11:
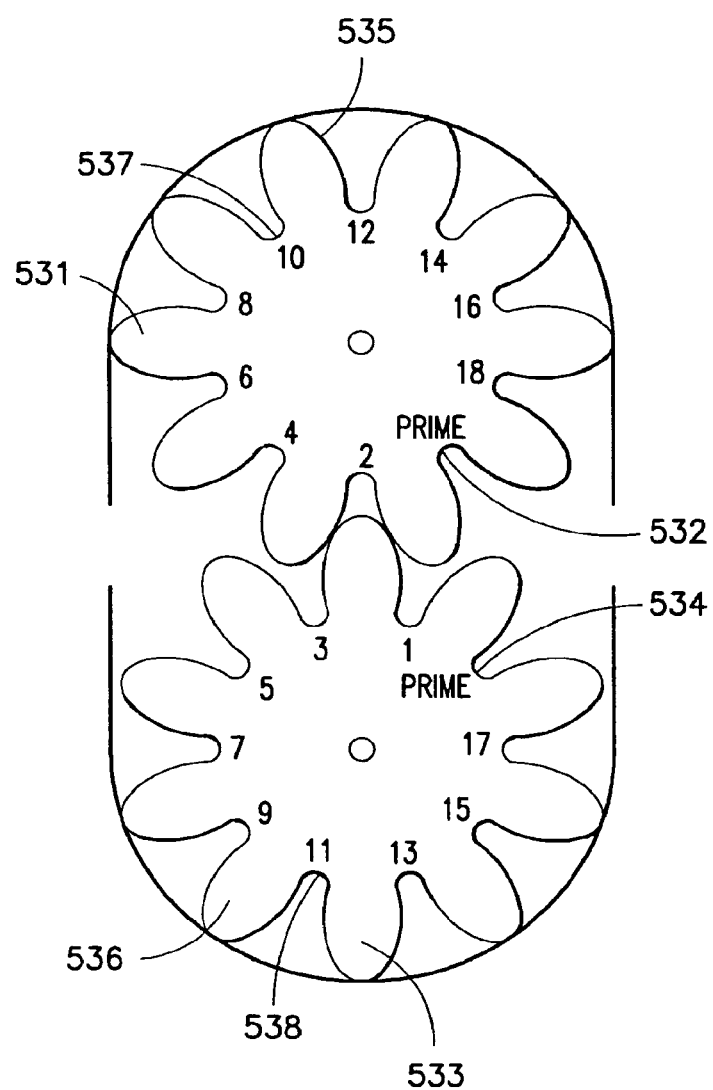
FIG. 11 is a schematic diagram of an exemplary gear arrangement of the gear pump assembly of FIG. 10.
Figure 12:
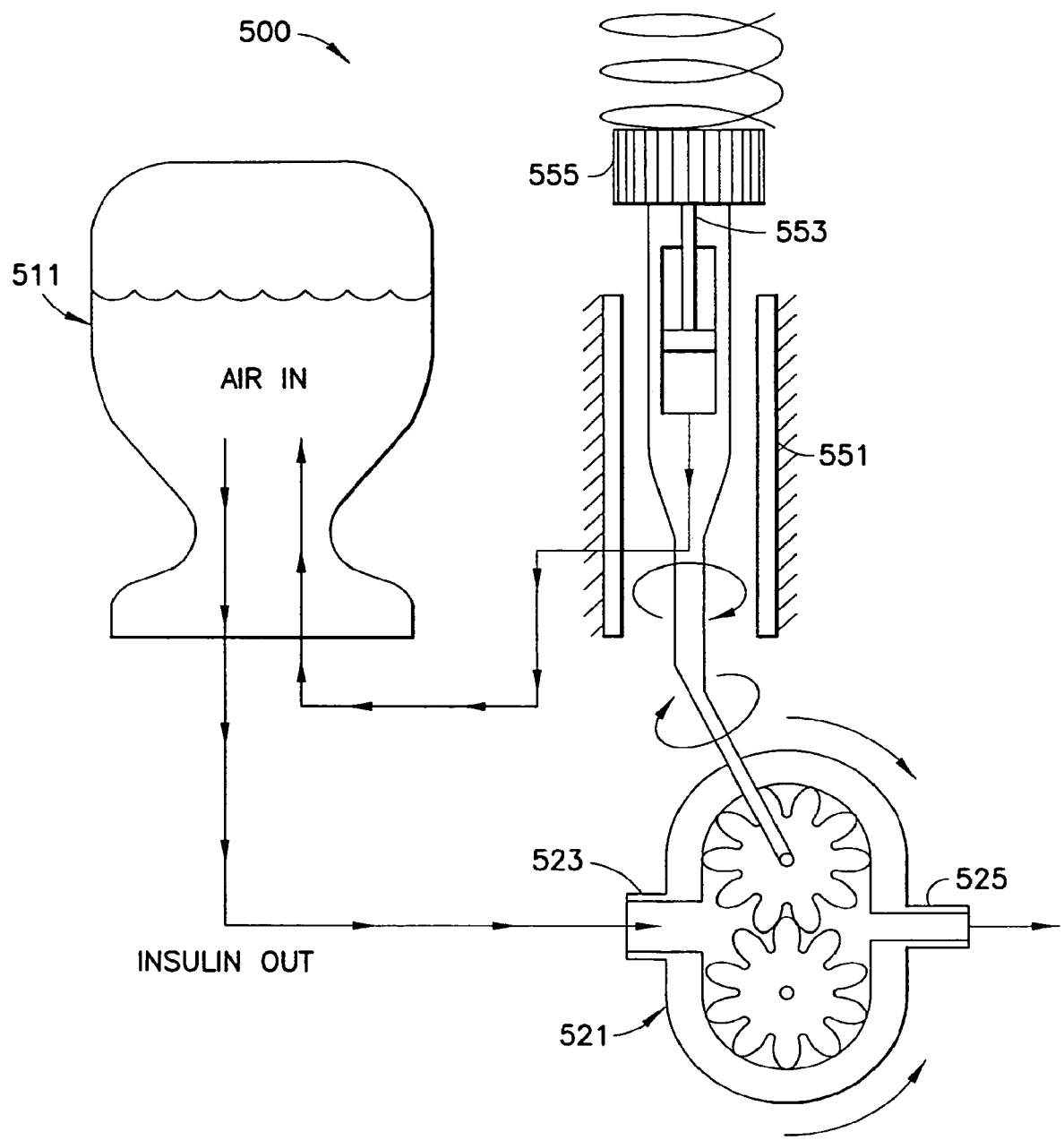
FIG. 12 is a schematic diagram of a gear pump assembly for a high pressure delivery system according to another exemplary embodiment of the present invention.

In another exemplary embodiment of the present invention shown in FIGS. 10-18, a high pressure drug delivery system 500 uses a vial 511 and a gear pump assembly 521 to meter the doses. As shown in FIGS. 10 and 12, the diameter of the dose input 523 to the gear pump assembly 521 is greater than the diameter of the gear pump assembly discharge 525, thereby providing a high pressure discharge. Each of the gears 531 and 533 of the gear pump assembly 521 may include a deep tooth 532 and 534 to provide a prime pocket, as shown in FIG. 11. The meshing of the gears 531 and 533 of the gear pump assembly 521 pumps fluid by creating a void to draw fluid into the gear teeth, carries the fluid between the teeth, and discharges the fluid with high pressure from the meshing of the teeth. Rigid gear teeth with tight tolerances allows for high pressure applications. A conventional gear pump assembly 521 is shown in FIG. 14.

Figure 13:
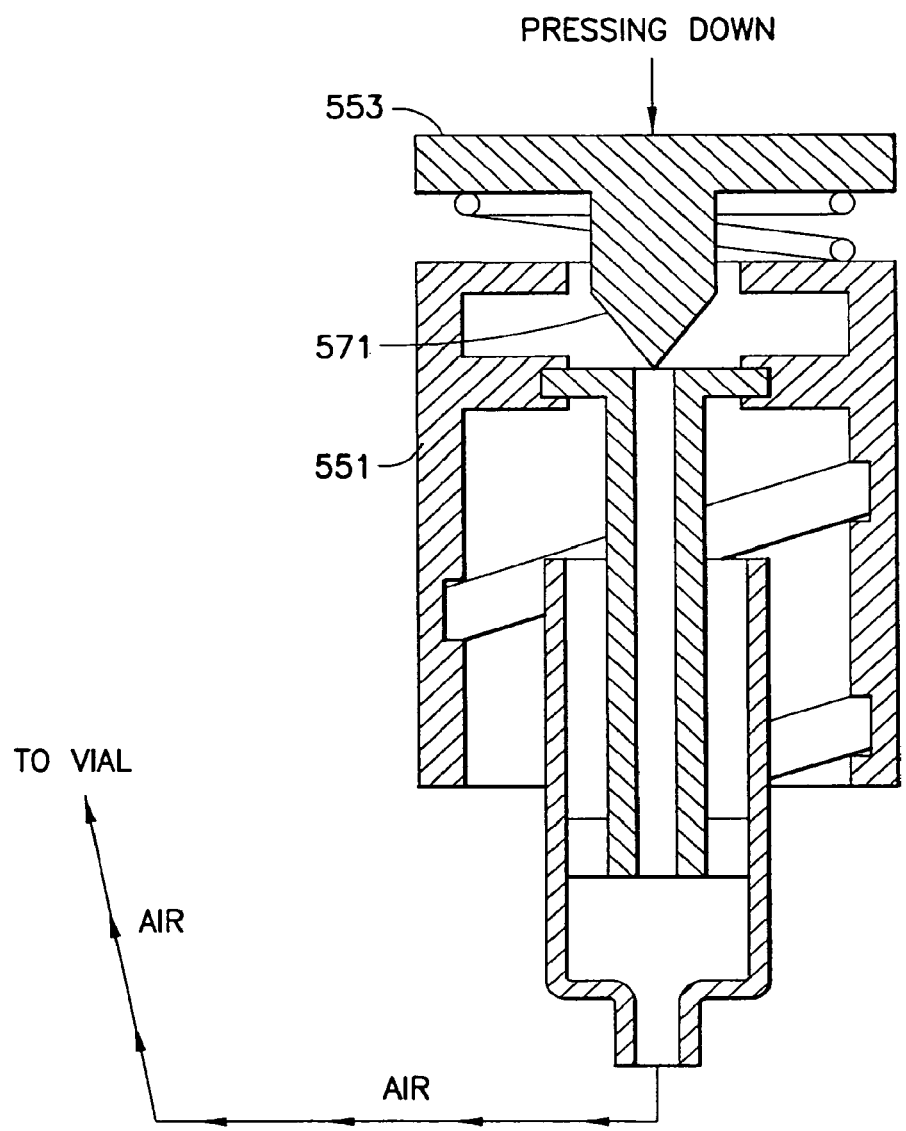
FIG. 13 is a schematic diagram of an exemplary syringe assembly of the high pressure delivery system of FIG. 12.

A dose is dialed with the dose screw 555 at the syringe 551 as shown in FIG. 12, which pulls up the syringe plunger 553, thereby loading the syringe with an "air dose." The syringe plunger 553 is then pushed down to close the syringe fill valve 571 and to force the air out of the syringe 551 into the vial 511. Pushing down the syringe plunger 553 also causes the gear pump assembly 521 to rotate, thereby drawing insulin out of the vial 511 and to the fluid connection path 561, such as a microneedle, at a high pressure. The high pressure drug delivery system 500 generates a high pressure using a gear pump assembly 521 that meters in ½ unit accuracy. The valving system 571 is on the "air side" not the "insulin side" of the delivery device, as shown in FIGS. 12 and 13. The vial 511 contains approximately a 3-4 week supply of insulin, thereby reducing the amount of waste.

In another exemplary embodiment of the high pressure drug delivery device 600 shown in FIG. 10, a syringe 651 that is filled with air through check valve 681 during dose setting, which is used to add pressure to the vial 611 as insulin is removed. After the dose is set and the user begins to inject, the air from the syringe 651 is pushed through a check valve 671 and into the vial 611 to prevent a vacuum from being formed in the vial. At the same time, the torque generated from the user's downward force on the syringe plunger 655 turns the gear pump assembly 521 that draws insulin out of the vial 611 and pumps it with high pressure to the fluid connection path 561.

Figures 15, 16:
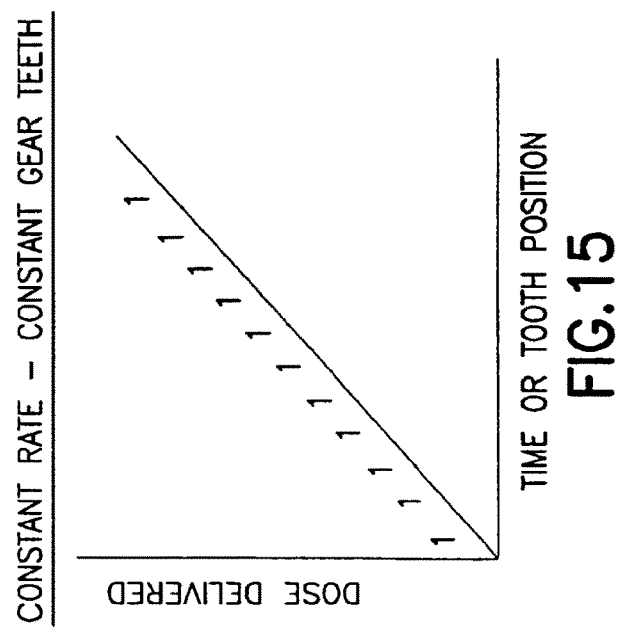
FIG. 15 is a graph of a constant rate dose delivery.
FIG. 16 is a table of the tooth position and the volume of the dose dispensed for the graph of FIG. 15.
Figures 17, 18:
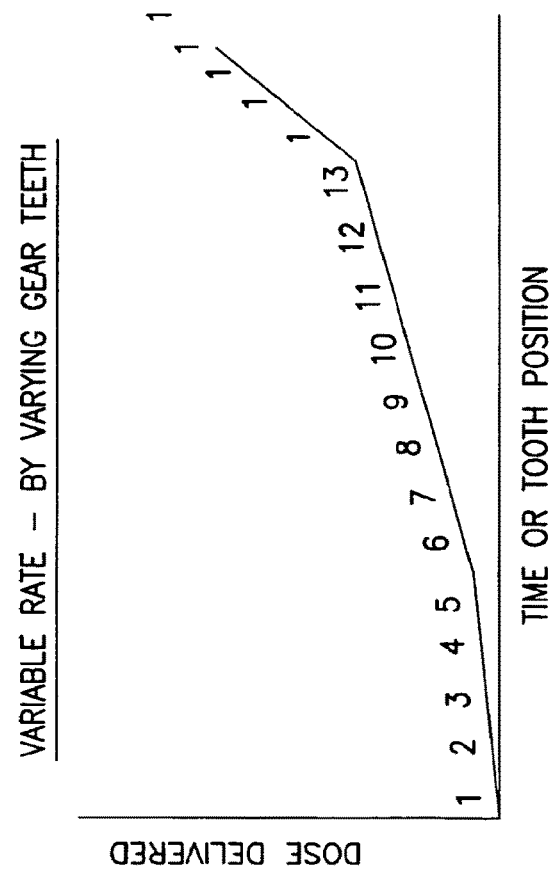
FIG. 17 is a graph of a variable rate dose delivery.
FIG. 18 is a table of the tooth position and the volume of the dose dispensed for the graph of FIG. 15.
Figure 19A:
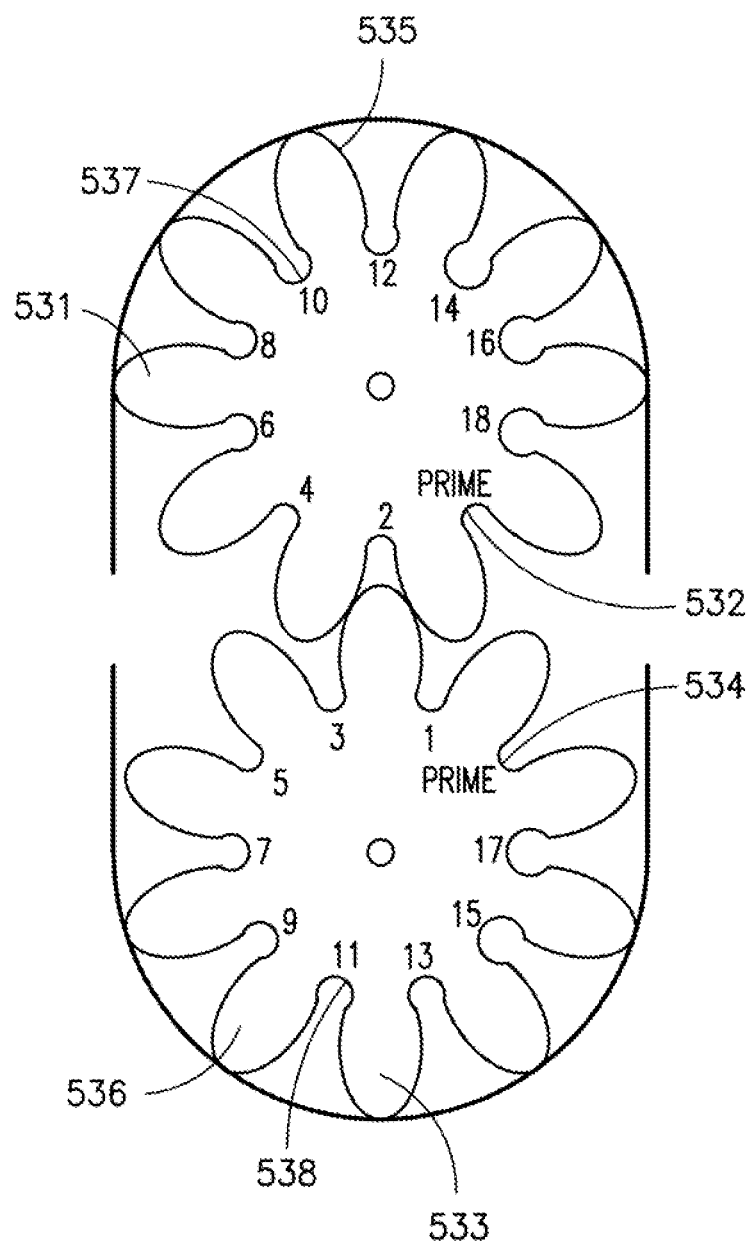
FIGS. 19A-19C are schematic diagrams of the gear arrangement of the gear pump assembly corresponding to the graph of FIG. 17 and the table of FIG. 18.
Figure 19B:
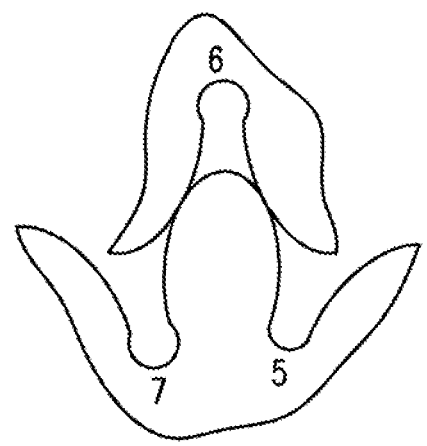
Figure 19C:
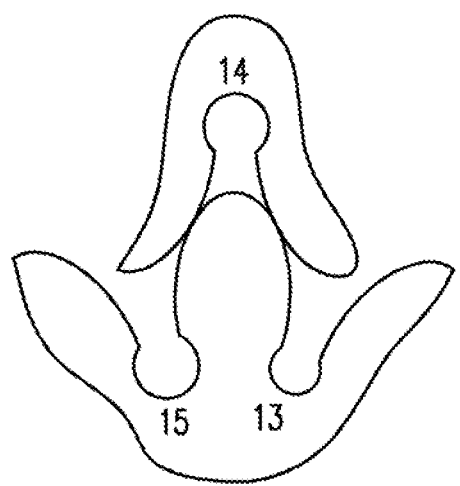

The gear pump assembly 521 allows the teeth 535 and 536 to be sized such that each drug volume space or pocket 537 and 538, which is the space between the teeth 535 and 536, respectively, may be ¼ or ½ unit volumes, or any other volume appropriate for metering and dose accuracy, as shown in FIGS. 15 and 16. Additionally, the first pockets 532 and 534 may be designated as "prime pockets" sized for the volume needed to prime the high pressure drug delivery system 500. Alternatively, the drug volume spaces or pockets 537 and 538 do not have to be equal for each tooth 535 and 536, respectively. For example, the first volumes after the prime may be smaller and then gradually increase in volume as the dose becomes larger, as shown in FIGS. 17, 18 and 19A-19C. This provides a variable rate control while maintaining accuracy, thereby providing slower infusion at the beginning of the injection and speeding up at the end. The mating of the variable rate injection with intradermal injection pressure may reduce overall backpressures and facilitate controlling the weeping or fluid leakage form the injection site.

The vial-based delivery device allows a larger 10 ml vial to be used instead of the smaller 3 ml cartridge, thereby increasing the available amount of doses and reducing the need for so many smaller cartridges. By using a gear pump assembly 521, the ability to provide high pressure is provided while also accurately metering doses. The gear pump assembly 521 may also provide variable rate control in connection with a consistent input, such as a torsion spring, driving the dose. Priming may be incorporated into the gear tooth layout by providing specifically sized teeth to hold the prime volume before the dose to ensure priming occurs.

As shown in FIGS. 17, 18 and 19A-19C, the high pressure drug delivery system 500 according to an exemplary embodiment of the present invention may use a variable rate gear pump assembly. A variable rate is achieved by providing smaller volumes between the first few gear teeth, and followed by larger volumes thereafter. For example, the four volumes between the first five gear teeth may amount to the first unit of insulin, with the remaining volumes being one unit each. The advantage of providing a slower rate of insulin flow in the beginning of the injection may lead to reduced back pressure during intradermal injection. Reduced or controlled back pressure may lead to more successful injections with respect to less leakage and reduced forces required for intradermal injection.

While exemplary embodiments have been chosen to illustrate the invention, it will be understood by those skilled in the art that various changes and modifications may be made therein without departing from the scope of the invention as defined in the appended claims.

What is claimed is:

1. A high pressure delivery system for delivering a medicament, comprising:
   a first chamber for storing a supply of the medicament;
   a gear pump assembly in fluid communication with the first chamber, said gear pump assembly having a dose inlet and a dose discharge, said dose inlet having a larger diameter than said dose discharge to provide a high pressure discharge; and
   a fluid connection path in fluid communication with the gear pump assembly for delivering the medicament to a high pressure area; wherein
   pockets formed between adjacent teeth of a first gear and adjacent teeth of a second gear of the gear pump assembly each have a volume at a cross section defined when respective teeth of the first gear and the second gear are fully engaged; and
   the pockets gradually increase in volume in the defined cross section such that a gradually increasing rate of medicament is delivered during the dose.

2. The high pressure delivery system for delivering a medicament according to claim 1, wherein:
   said first chamber comprises a medicament cartridge and said fluid connection path comprises a needle.

3. The high pressure delivery system for delivering a medicament according to claim 1, wherein:
   the gear pump assembly includes one or more gear teeth that contact the medicament from the first chamber.

4. The high pressure delivery system for delivering a medicament according to claim 1, wherein:
   the pockets are formed in meshing portions between the teeth of the first and the second gears of the gear pump.

5. The high pressure delivery system for delivering a medicament according to claim 1, wherein:
   a first pocket formed between adjacent teeth of the first gear and a second pocket formed between adjacent teeth of the second gear primes the high pressure drug delivery system; and
   subsequent pockets formed between adjacent teeth of the first and the second gears, respectively, gradually increase in volume.

6. The high pressure delivery system for delivering a medicament according to claim 1, wherein:
   a second chamber is in fluid communication with said first chamber.

7. The high pressure delivery system for delivering a medicament according to claim 1, wherein:
   the gear pump assembly provides variable rate control while receiving a consistent input driving the medicament.

8. The high pressure delivery system for delivering a medicament according to claim 7, wherein:
   the consistent input includes a torsion spring.

* * * * *